US010781494B2

(12) United States Patent
Nelson et al.

(10) Patent No.: US 10,781,494 B2
(45) Date of Patent: Sep. 22, 2020

(54) METHODS OF DETECTING *LISTERIA* FROM AN ENVIRONMENTAL SAMPLE

(71) Applicant: Neogen Corporation, Lansing, MI (US)

(72) Inventors: John Nelson, Bath, MI (US); Preetha Biswas, Okemos, MI (US); Lei Zhang, Okemos, MI (US); Mark A. Mozola, Placitas, NM (US); Lisa Pinkava, Lansing, MI (US); David Brookman, Montreal (CA); Edan Robert Hosking, Lansing, MI (US)

(73) Assignee: NEOGEN CORPORATION, Lansing, MI (US)

( * ) Notice: Subject to any disclaimer, the term of this patent is extended or adjusted under 35 U.S.C. 154(b) by 0 days.

(21) Appl. No.: 15/556,068

(22) PCT Filed: Sep. 13, 2016

(86) PCT No.: PCT/US2016/051426
§ 371 (c)(1),
(2) Date: Sep. 6, 2017

(87) PCT Pub. No.: WO2017/048664
PCT Pub. Date: Mar. 23, 2017

(65) Prior Publication Data
US 2018/0179582 A1 Jun. 28, 2018

Related U.S. Application Data

(60) Provisional application No. 62/218,678, filed on Sep. 15, 2015.

(51) Int. Cl.
*C12Q 1/689* (2018.01)
*C12Q 1/68* (2018.01)
*C12P 19/34* (2006.01)

(52) U.S. Cl.
CPC ....... *C12Q 1/689* (2013.01); *C12Q 2531/101* (2013.01); *G01N 2333/195* (2013.01)

(58) Field of Classification Search
None
See application file for complete search history.

(56) References Cited

U.S. PATENT DOCUMENTS 7,575,864 B2  8/2009  Bedzyk et al.
2014/0093883 A1  4/2014  Maples et al.

FOREIGN PATENT DOCUMENTS

CN   103146835    6/2013
WO   WO2009/012246 A3  1/2009

OTHER PUBLICATIONS

Gasanov et al., "Methods for the isolation and identification of *Listeria* spp. and Listeria monocytogenes: a review", FEMS Microbiology Reviews, vol. 29, pp. 851-875. (Year: 2005).*
Grady et al., "Rapid real-time PCR detection of Listeria monocytogenes in enriched food samples based on the ssrA gene, a novel diagnostic target", Food Microbiology, vol. 25, pp. 75-84. (Year: 2008).*
Wendorf et al., "Validation of the ANSR(R) Listeria Method for Detection of *Listeria* spp. in Environmental Samples," Journal of AOAC International, vol. 96, No. 6, pp. 1414-1424. (Year: 2013).*
Definition of "expression", [retrieved on-line, retrieval date May 20, 2019, retrieved from: https://www.meriam-webster.com/dictionary/expression] (Year: 2019).*
Birmpa, A., et al. Evaluation of two loop-mediated isothermal amplication methods for the detection of *Salmonella enteritidis* and Listeria monocytogenes in artificially contaminated ready-to-eat fresh produce. Italian Journal of Food Safety 2015; 4:5383 pp. 129-136.
International Search Report and Written Opinion for PCT/US2016/051426 dated Nov. 30, 2016.
Presentation by Dupont entitled BAX® System dated Apr. 2010, 29 pages.
Product brochure. Dupont Qualicon BAX System 2007—2 pages.
Evaluation of the Thermo Scientific SureTect *Listeria* Species Assay. Journal of AOAC International vol. 97, No. 2, 2014, pp. 521-538.
Fykse, E.M., et al. Detection of Vibrio cholerae by Real-Time Nucleic Acid Sequence-Based Amplication. Applied and Environmental Mecrobiology, vol. 73, No. 5, Mar. 2007, pp. 1457-1466.
Caballero, et al. Validation of the ANSR Listeria Method for Detection of *Listeria* spp. In Selected Foods. Journal of AOAC International vol. 98, No. 5, 2015 pp. 1290-1300.
O'Grady, Justin, et al. tmRNA—a novel high-copy-number RNA diagnostic target—its application for *Staphylococcus aureus* detection using real-time NASBA. FEMS Microbiol Lett 301 (2009) pp. 218-223.
Wendorf, et al. Validation of the ANSR Listeria Method for Detection of *Listeria* spp. in Envinromental Samples. Journal of AOAC International vol. 96, No. 6, 2013, pp. 1414-1424.
Cappillino, et al. Sample6 Detect/L: An In-plant, In-shift, Enrichment-free Listeria Environmental Assay. Journal of AOAC International, vol. 98, No. 2, Mar. 2015 pp. 436-444.
Yang, et al. Roka Listeria Detection Method Using Transcription Mediated Amplification to Detect *Listeria* Species in Select Foods and Surfaces. Journal of AOAC International vol. 95, No. 6, 2012, pp. 1672-1688.
Loessner, Martin J., et al. A New Procedure for Efficient Recovery of DNA, RNA, and Proteins from Listeria Cells by Rapid Lysis with a Recombinant Bacteriophage Endolysin. Applied and Environmental Microbiology, Mar. 1995, p. 1150-1152, vol. 61, No. 3.

(Continued)

*Primary Examiner* — Young J Kim
(74) *Attorney, Agent, or Firm* — Honigman LLP; Douglas H. Siegel; Jonathan P. O'Brien

(57) ABSTRACT

The present invention relates to the identification of microorganisms from an environmental sample, and in particular to the rapid identification of *Listeria* spp. The methods and kits described herein provide a method of detecting *Listeria* spp. without the need for an enrichment step.

12 Claims, 9 Drawing Sheets

(56) References Cited

OTHER PUBLICATIONS

Livezey, et al. A New General of Food-Borne Pathogen Detection Based on Ribosomal RNA. Annu. Rev. Food Sci. Technol. 2013, 4:313-325.
Wang, et al. Rapid Detection of Listeria monocytogenes in Raw Milk with Loop-Mediated Isothermoal Amplication and Chemosensor. Journal of Food Science, vol. 76(9), 2011, pp. M611-M615.
Ye, et al. Rapid detection of viable Listeria monocytogenes in chilled pork by real-time reverse-transcriptase PCR. Science Direct, vol. 25(1) 2012 pp. 117-124.
Navas, Jamie, et al. "Simultaneous Detection of Listeria monocytogenes in Chicken Meat Enrichments by PCR and Reverse-Transcription PCR without DNA/RNA Isolation" Journal of Food Protection, vol. 68, No. 2, 2005, pp. 407-410.

\* cited by examiner

Figure 2.

Test Site 1

| | Culture | | |
|---|---|---|---|
| | | + | − |
| ANSR | + | 2 | 2 |
| | − | 0 | 41 |
| N = 45 | | | |

Invalid = 5

Figure 5.

Test Site 4

| N = 38 | Culture | | |
|---|---|---|---|
| | | + | − |
| ANSR | + | 0 | 0 |
| | − | 0 | 38 |

Invalid = 0

Figure 6.

Test Site 5

N = 44

Culture

|  | + | − |
|---|---|---|
| + | 10 | 4 |
| − | 6 | 24 |

ANSR

Invalid = 0

METHODS OF DETECTING *LISTERIA* FROM AN ENVIRONMENTAL SAMPLE

CROSS-REFERENCE TO RELATED APPLICATIONS

This Patent Application is a 35 U.S.C. § 371 United States National Phase Stage of, and claims priority to, PCT International Application No. PCT/US2016/051426 filed Sep. 13, 2016, which claims the benefit under 35 U.S.C. § 119 of U.S. Provisional Ser. No. 62/218,678, filed Sep. 15, 2015. The entire contents of the aforementioned application are incorporated herein by reference.

TECHNICAL FIELD

The present invention relates to the identification of microorganisms from an environmental sample, and in particular to the rapid identification of *Listeria* spp.

BACKGROUND

*Listeria* spp. are ubiquitous bacteria widely distributed in the environment. Among the species of *Listeria*, only *Listeria monocytogenes* is commonly pathogenic for humans. However, some other species of *Listeria* are pathogenic. *Listeria ivanovii*, for example, is a pathogen of mammals, specifically ruminants, and while not pathogenic for humans, it is pathogenic for animals.

*Listeria* is the causative agent of the relatively rare bacterial disease, listeriosis, which affects primarily pregnant women, newborns, adults with weakened immune systems, and the elderly. Food-borne transmission constitutes the main route of acquisition of listeriosis. *Listeria* can be found in soil, which can lead to vegetable contamination; however, animals can also be carriers.

Listeriosis is a serious disease for humans; the two main clinical manifestations are sepsis and meningitis. Meningitis is often complicated by encephalitis, or meningoencephalitis, a pathology that is unusual for bacterial infections. Although human listeriosis occurs only sporadically, several outbreaks have been observed in recent years. Despite efficient antibiotic therapy, listeriosis represents a public health problem due to fatality in up to 30% of cases.

*Listeria* is an extremely hardy organism that can survive in the cold for many years in naturally contaminated sources. *Listeria* spp. can be found throughout the environment, and therefore, there is a potential for contamination in a wide variety of foods. Meat, eggs, chicken, seafood, dairy products and vegetables have all been identified as sources of *Listeria* outbreaks. Food processors, packaging facilities and public health officials have recognized *Listeria* spp. as an indicator of contamination of food, water and environmental conditions, thus procedures exist for monitoring foods, water and the environment for contamination requiring measurement of *Listeria* spp. However, rapid detection and identification of *Listeria* spp. is essential to the food industry and existing methods are dependent on enrichment of the sample to increase the concentration of target organisms, or other types of prolonged incubation steps required to increase the concentration of target molecules to detectable levels. As such, detection can take up to 24-48 hours. Some methods purport not to require an enrichment step; however, the methods still require long incubation periods of up to 6-8 hours.

A specific example of such a system is Sample6 DETECT. While the procedure is said to be "enrichment-free," it uses a phage to infect specific bacterial cells and amplify a signal, which requires an incubation of 4-8 hours. Likewise, the DuPont BAX® system is referred to as a "no enrichment" *Listeria* assay, but requires a "resuscitation" step of 4 hours.

Accordingly, there is a need for a method and diagnostic tool that rapidly detects and identifies *Listeria* spp. in environmental samples. These needs and other needs are satisfied by the devices, methods, and kits of the present invention.

SUMMARY OF THE INVENTION

The purpose of the method is to provide users with a means to assay for the presence of *Listeria* spp. in environmental samples from food production, food processing or food service sites without enrichment or incubation prior to performing the diagnostic assay itself. In one embodiment, the method utilizes the ANSR® *Listeria* spp. isothermal nucleic acid amplification assay in conjunction with a modified sample lysis procedure. In some embodiments, the entire collected sample is subjected to the lysis procedure, which is conducted in a small volume of lysis buffer. A benefit of the method is that results can be obtained in approximately 50 minutes from sample collection, compared to several hours for methods of lower sensitivity that are dependent on enrichment of the sample to increase the concentration of target organisms, or other types of prolonged incubation steps required to increase the concentration of target molecules to detectable levels.

In some embodiments, the invention provides a method for detecting *Listeria* spp. in an environmental sample, the method comprising the steps of: collecting an environmental sample with a collection device; expressing the collection device in lysis buffer; and performing a pathogen diagnostic assay that targets bacterial RNA sequences for detection and amplification of *Listeria* RNA in the sample. In some embodiments, the environmental sample is positive for *Listeria* RNA. In some embodiments, the environmental sample is negative for *Listeria* RNA.

In some embodiments, the pathogen diagnostic assay utilizes isothermal amplification of the RNA. In some embodiments, the pathogen diagnostic assay is the ANSR® *Listeria* spp. isothermal nucleic acid amplification assay.

In some embodiments, the collection device is a swab, a q-tip or a sponge. In some embodiments, the collection device is pre-moistened with letheen broth.

In some embodiments, the time from collection of the sample to completion of the pathogen diagnostic assay is 1 hour or less.

In some embodiments, the assay is of sufficient sensitivity to detect as little as 1-2 CFU in the environmental sample without enrichment of the sample.

In some embodiments, the volume of lysis buffer is about 1.0 ml. In some embodiments, about 0.5 ml of the sample in lysis buffer is used for the pathogen diagnostic assay.

In some embodiments, the invention provides a kit for detecting the presence of *Listeria* spp. in an environmental sample comprising a container, the container comprising: a collection device for collecting an environmental sample; lysis buffer for expressing the collection device; and a pathogen diagnostic assay that targets bacterial RNA sequences for detection and amplification of *Listeria* RNA in the sample.

In some embodiments of the kit, the collection device is a swab. In some embodiments, the collection device is pre-moistened with letheen broth.

In some embodiments of the kit, the container further comprises sample tubes.

BRIEF DESCRIPTION OF THE DRAWINGS

These and other features, aspects, and advantages of the present invention may be better understood when the following detailed description is read with reference to the accompanying drawings.

FIG. 2 depicts results for Test Site 1.

FIG. 5 depicts results for Test Site 4

FIG. 6 depicts results for Test Site 5.

DETAILED DESCRIPTION

Figure 1:
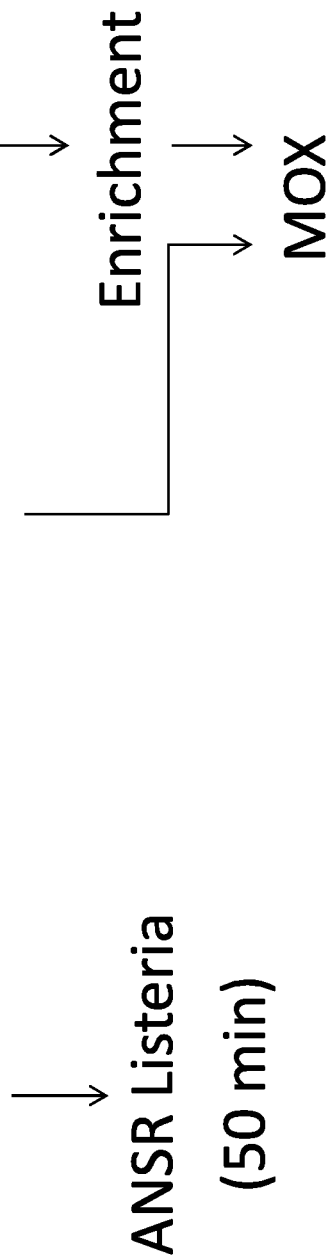
FIG. 1 depicts the key steps in the Reference Method and Experimental Method.
Figure 3:
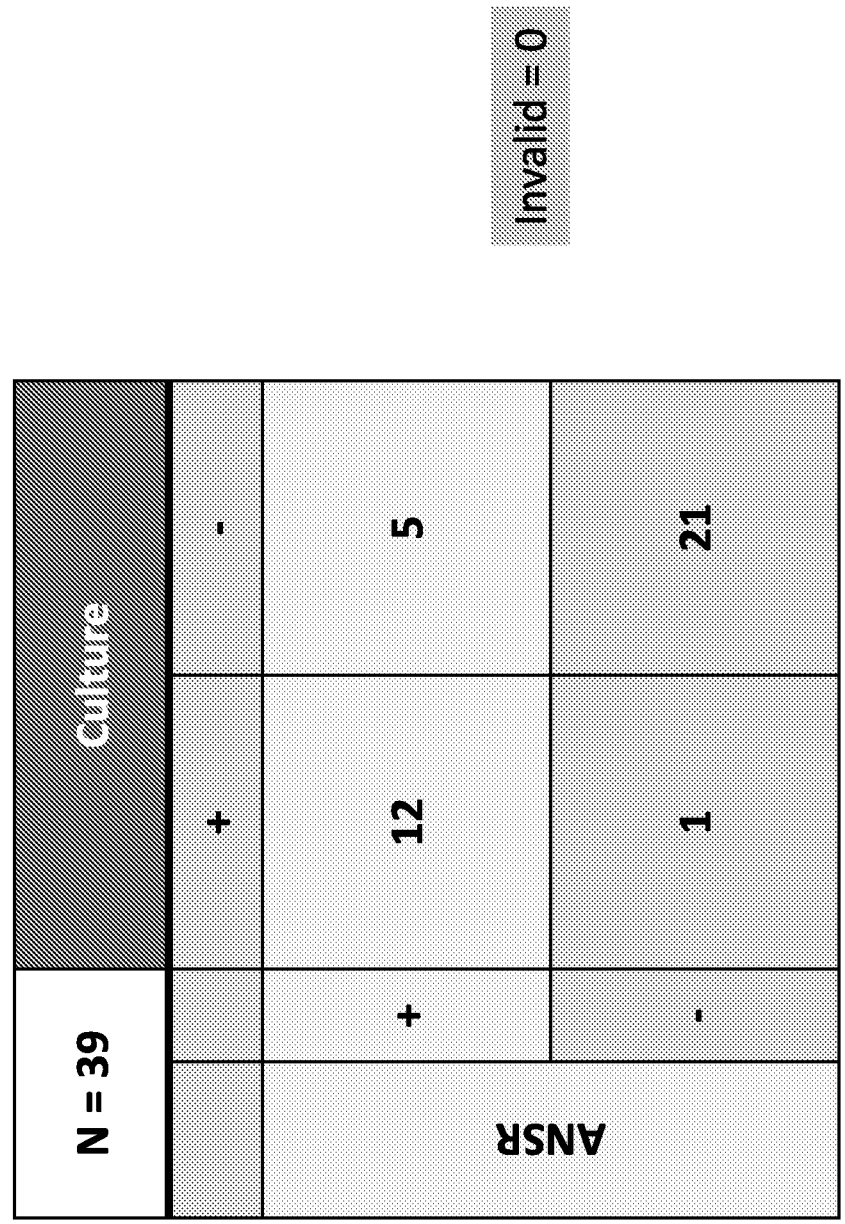
FIG. 3 depicts results for Test Site 2.
Figure 4:
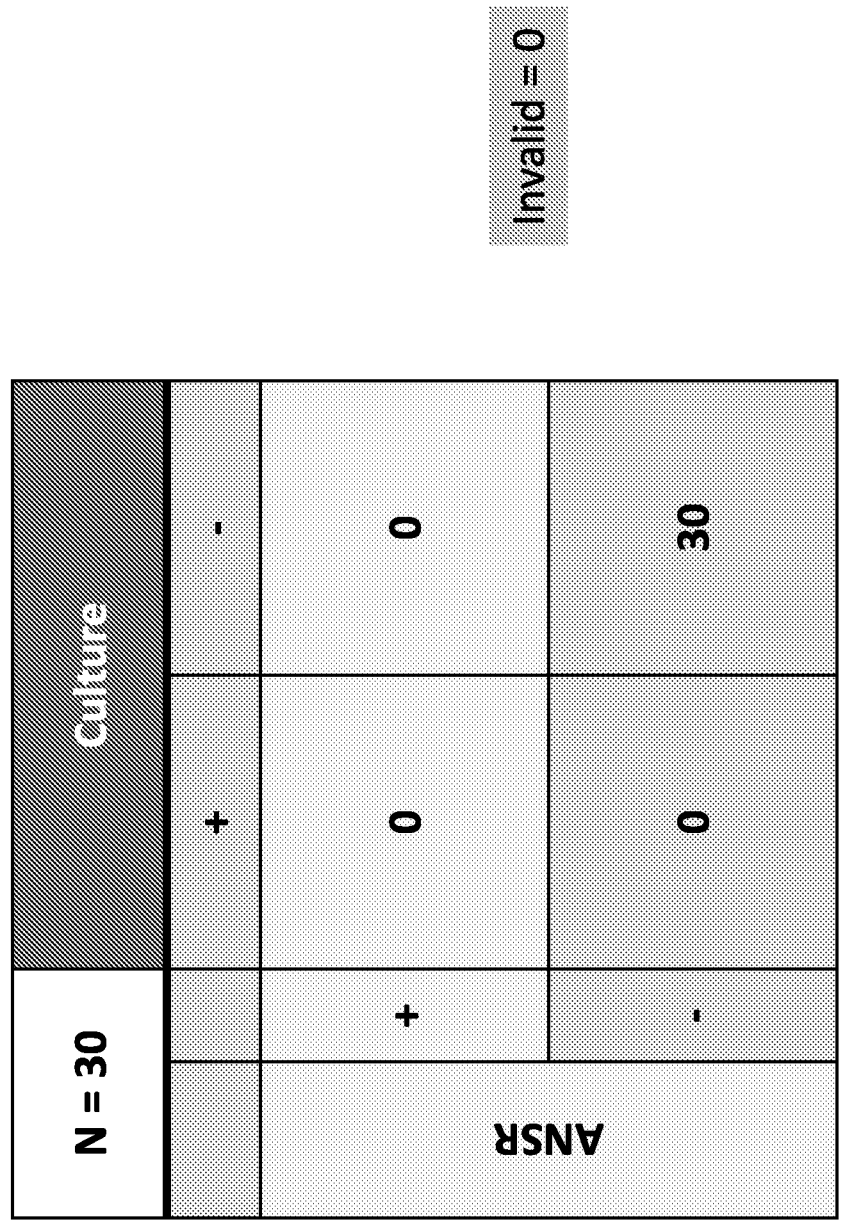
FIG. 4 depicts results for Test Site 3.
Figure 7:
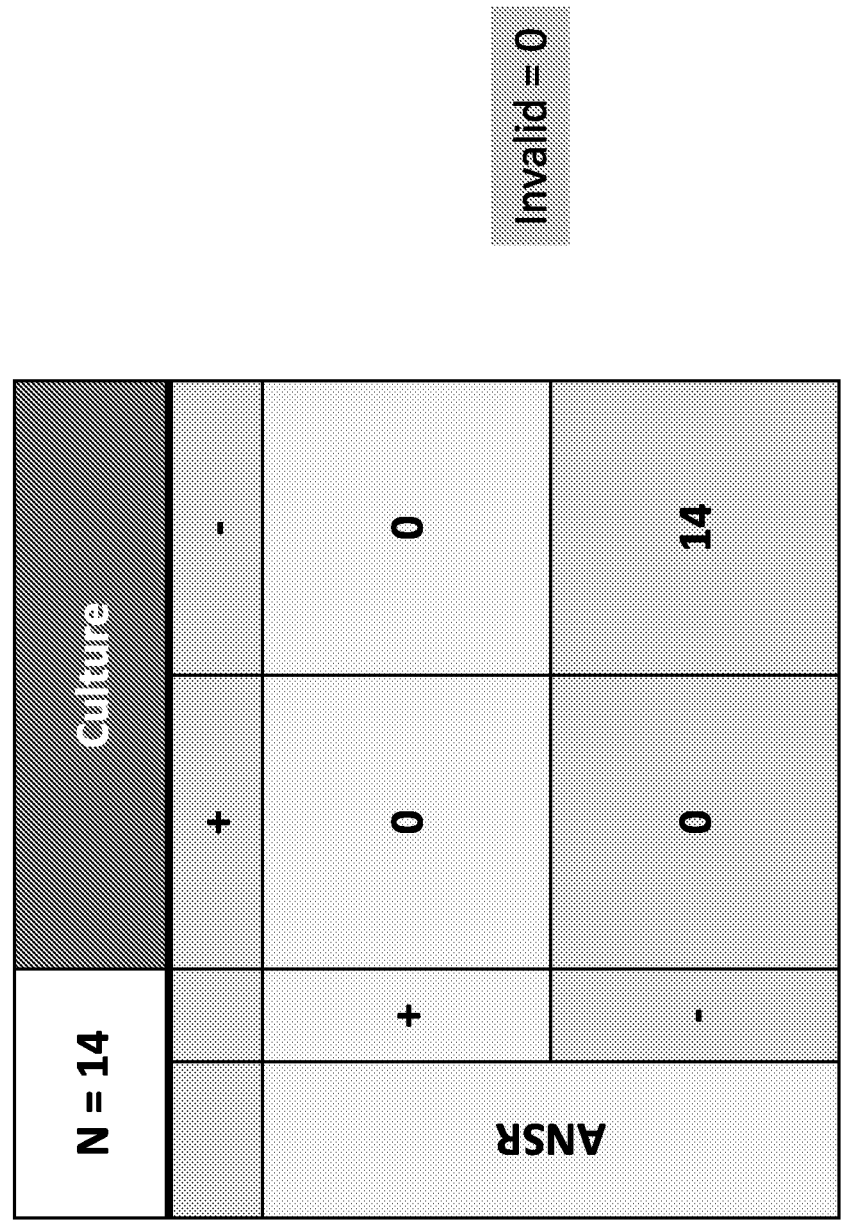
FIG. 7 depicts results for Test Site 6.
Figure 8:
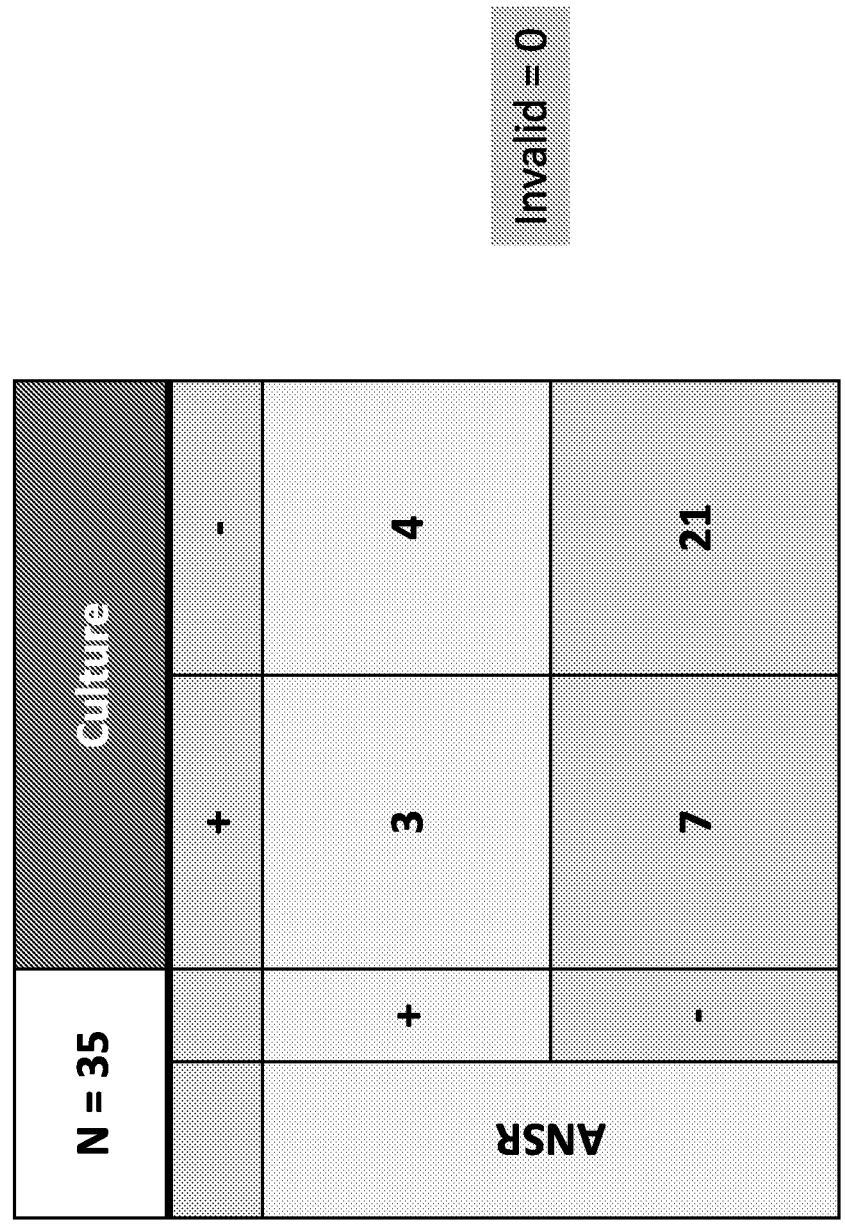
FIG. 8 depicts results for Test Site 7.
Figure 9:
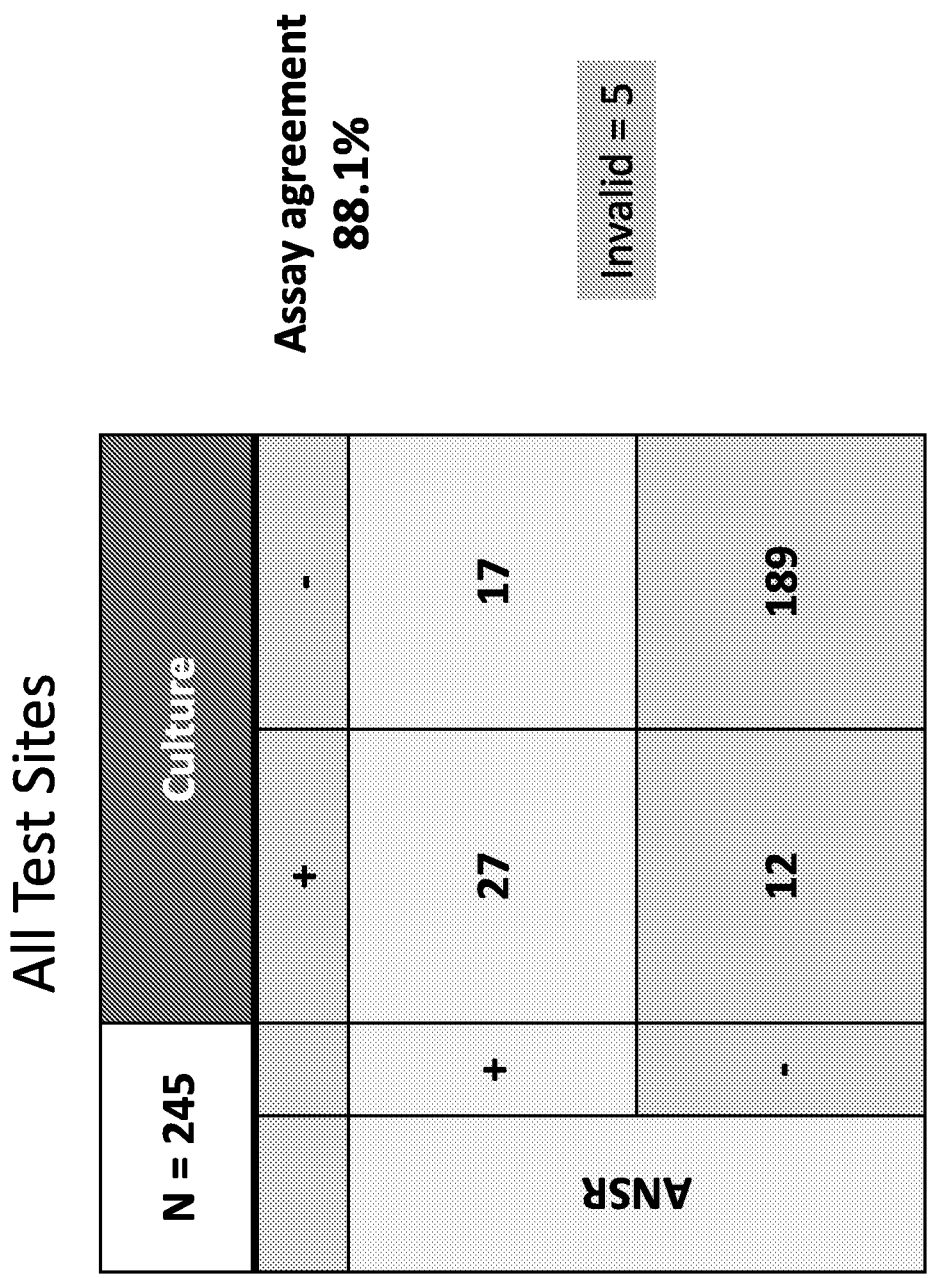
FIG. 9 depicts composite results for all test sites.

In the following description, numerous specific details are given to provide a thorough understanding of the embodiments. The embodiments can be practiced without one or more of the specific details, or with other methods, components, materials, etc. In other instances, well-known structures, materials, or operations are not shown or described in detail to avoid obscuring aspects of the embodiments.

Reference throughout this specification to "one embodiment," "an embodiment," or "embodiments" means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Unless indicated otherwise, when a range of any type is disclosed or claimed, it is intended to disclose or claim individually each possible number that such a range could reasonably encompass, including any sub-ranges encompassed therein. Moreover, when a range of values is disclosed or claimed, which Applicants intend to reflect individually each possible number that such a range could reasonably encompass, Applicants also intend for the disclosure of a range to reflect, and be interchangeable with, disclosing any and all sub-ranges and combinations of sub-ranges encompassed therein.

Methods and reagents for isothermal detection and amplification of RNA are described in International Patent Application Publication No. WO 2009/012246, which is incorporated by reference herein in its entirety. Briefly, the methods of amplifying nucleic acid target sequences rely on nicking and extension reactions to amplify shorter sequences in a shorter timeframe than traditional amplification reactions, such as, for example, strand displacement amplification reactions. Embodiments of the invention include, for example, reactions that use only two templates to amplify a target sequence, one or two nicking enzymes, and a polymerase, under isothermal conditions. In exemplary embodiments, the polymerase and the nicking enzyme are thermophilic, and the reaction temperature is significantly below the melting temperature of the hybridized target region. The nicking enzyme nicks only one strand in a double-stranded duplex, so that incorporation of modified nucleotides is not necessary as in the case of conventional strand displacement amplification. An initial heat denaturation step is not required for the methods of the present invention. Due to the simplicity of the reaction, in exemplary embodiments, the reaction is very easy to perform, requires no special equipment, such as a thermocycler, and can amplify 20-30mer products 108 to 1010 fold from genomic DNA in only about 2.5 to about 10 minutes. The method is able to amplify RNA during a simultaneous reverse transcription step.

The ANSR® Listeria assay is an isothermal detection system that targets ribosomal RNA (rRNA), a high copy number target. Lysis of even a single Listeria cell can release on the order of 1,000 to 10,000 copies of rRNA. Since the lysis reaction is performed in a small volume, target concentration is sufficiently high that a 5-50 uL aliquot of the lysate subsequently transferred to the ANSR® assay reagent tube will contain a sufficient number of target rRNA molecules for detection.

One of ordinary skill in the art would recognize that various other pathogen diagnostic assays that target bacterial RNA sequences for detection and amplification of Listeria RNA in the sample may be used in the invention. In some embodiments, the pathogen diagnostic assay is the Atlas® Listeria LSP Detection Assay (Roka Bioscience). In some embodiments, the pathogen diagnostic assay is the BAX® System Real-Time PCR Assay for Genus Listeria (DuPont).

Providing a sample to be tested may comprise providing a sample that is suspected of containing a target microorganism. The sample can be any sample that may include a target microorganism as defined herein. Nonlimiting examples of suitable samples include environmental samples (e.g., surface swabs/sponges, soil, sediments, fomites), food (e.g., raw materials, in-process samples, and finished-product samples), beverages, clinical/veterinary samples (e.g., blood, serum, plasma, urine, sputum, tissue, mucous, feces, wound exudate, pus, cerebrospinal fluid), and water (e.g., surface water, potable water, process water).

In some embodiments, the presence or absence of a target microorganism can be analyzed in a test sample that is derived from a variety of food, beverage, or food- or beverage-processing environmental sources. Non-limiting examples of food sources include raw or processed meat, raw or processed fruits or vegetables, non-fluid dairy products (e.g., cheese, butter, and ice cream), nuts, spices, ingredients, and syrups. Non-limiting examples of beverage sources include potable water, fruit or vegetable juices, milk, and fermented beverages.

Pasteurized food or beverages may also be suitable sources. Non-limiting examples of food- or beverage-processing environmental samples include food-handling surface samples (e.g., conveyor belts, blades, cutting surfaces, mixing equipment surfaces, filters, storage containers), room samples (e.g., walls, floors, drains, ventilation equipment), and cleaning equipment (e.g., hoses, cleaning tools).

In some embodiments, the presence or absence of a target microorganism can be analyzed in a sample that is derived from a variety of human or animal sources, such as a physiological fluid, e.g., blood, saliva, ocular lens fluid, synovial fluid, cerebral spinal fluid, pus, sweat, exudate, urine, mucus, lactation milk, or the like. Further, the test sample may be derived from a body site, e.g., wound, skin, nares, scalp, nails, etc.

Samples of particular interest from human or animal sources include mucus-containing samples, such as nasal samples (from, e.g., anterial nares, nasopharyngeal cavity, nasal cavities, anterior nasal vestibule, etc.), as well as samples from the outer ear, middle ear, mouth, rectum, vagina, or other similar tissue. Examples of specific musosal tissues include buccal, gingival, nasal, ocular, tracheal, bronchial, gastrointestinal, rectal, urethral, ureteral, vaginal, cervical, and uterine mucosal membranes.

Besides physiological fluids, other test samples may include other liquids as well as solid(s) dissolved in a liquid medium. Samples of interest may include process streams, water, soil, plants or other vegetation, air, surfaces (e.g., contaminated surfaces), and the like. Samples can also include cultured cells. Samples can also include samples on or in a device comprising cells, spores, or enzymes (e.g., a biological indicator device).

Suitable samples for methods of the present disclosure can include certain solid samples. Solid samples may be disintegrated (e.g., by blending, sonication, homogenization) and may be suspended in a liquid (e.g., water, buffer, broth). In some embodiments, a sample-collection device (e.g., a swab, a sponge) containing sample material may be used in the method.

Alternatively, the sample material may be eluted (e.g., rinsed, scraped, expressed) from the sample-collection device before using the sample material in the method. In some embodiments, liquid or solid samples may be diluted in a liquid (e.g., water, buffer, broth).

The sample may comprise an indicator microorganism, as described herein. The indicator microorganism can be indicative of contamination (e.g., fecal contamination), infection (e.g., infection with a pathogenic microorganism), or an indicator of general sanitation (e.g., any aerobic microorganism). The indicator microorganism further can be a target microorganism.

Microorganisms of particular interest, which may be of interest as an indicator organism or a target microorganism, include prokaryotic and eukaryotic organisms, particularly Gram positive bacteria, Gram negative bacteria, fungi, mycoplasma, and yeast. Particularly relevant organisms include members of the family Enterobacteriaceae, or the family Micrococcaceae or the genera *Staphylococcus* spp., *Streptococcus* spp., *Pseudomonas* spp., *Enterococcus* spp., *Salmonella* spp., *Legionella* spp., *Shigella* spp. *Yersinia* spp., *Enterobacter* spp., *Escherichia* spp., *Bacillus* spp., *Listeria* spp., *Vibrio* spp., *Corynebacteria* spp. as well as, *Aspergillus* spp., *Fusarium* spp., and *Candida* spp. Particularly virulent organisms include *Staphylococcus aureus* ( ), *S. epidermidis*, *Streptococcus pneumoniae*, *S. agalactiae*, *S. pyogenes*, *Enterococcus faecalis*, *Bacillus anthracis*, *Pseudomonas aeruginosa*, *Escherichia coli*, *Aspergillus niger*, *A. fumigatus*, *A. clavatus*, *Fusarium solani*, *F. oxysporum*, *F. chlamydosporum*, *Listeria monocytogenes*, *Listeria ivanovii*, *Vibrio cholera*, *V parahemolyticus*, *Salmonella cholerasuis*, *S. typhi*, *S. typhimurium*, *Candida albicans*, *C. glabrata*, *C. krusei*, *Cronobacter sakazakii*, Gram positive and Gram negative bacteria are of particular interest. Of particular interest are Gram positive bacteria, such as *Listeria monocytogeness*.

Collection Device

Inoculating the collection device can be done by a variety of methods that are known in the art. Nonlimiting examples of suitable inoculation methods include pour-plate techniques, surface inoculation techniques, streak-plating techniques, swab-plating techniques, and surface contact-plating techniques (e.g., Rodac plating methods). Filter membrane plating techniques may be used in the present method, provided that the membrane filter does not substantially interfere with the reaction between the microorganisms and the indicator systems or interfere with the observation of the indicator systems.

In some embodiments, the collection device is a swab. The swab may be comprised of cotton or polyester and may be pre-moistened in solution. In some embodiments, the swab is pre-moistened in Letheen broth. In other embodiments, the swab is pre-moistened in Neutralizing Buffer, Buffered Peptone Water, or culture medium.

In some embodiments, the swab is provided as a polypropylene tube and cap containing a Letheen broth solution and a swab with polypropylene shaft and polyester fiber tip. In some embodiments, the swab is sold as Veriswab™ Samplers with Letheen Broth (World Bioproducts LLC). In some embodiments, the swab is sold as 3M™ Swab-Sampler with Letheen Broth. In some embodiments, the swab is sold as 3M™ Quick Swab.

Definitions

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

As used herein, "a," "an," "the," "at least one," and "one or more" are used interchangeably. Thus, for example, a microorganism can be interpreted to mean "one or more" microorganisms.

The term "and/or" means one or all of the listed elements or a combination of any two or more of the listed elements.

As used herein, the terms "*Listeria*" and "*Listeria* spp." are used interchangeably and refer to all species of the Gram-positive rod shaped bacteria, including, but not limited to, *L. grayi*, *L. innocua*, *L. ivanovii*, *L. monocytogenes*, *L. seeligeri*, *L. welshimeri*.

As used herein, "ANSR® for *Listeria*" and "ANSR® for *Listeria monocytogenes*" refer to an isothermal amplification reaction test method that exponentially amplifies the DNA of any bacteria present in samples to detectable levels in only minutes.

As used herein, "lysis buffer" refers to a liquid buffer containing components to break open bacterial cells and release nucleic acid. The lytic components may be, but are not limited to, detergents, enzymes or denaturing salts. In some embodiments, the lysis buffer is the ANSR™ Lysis Buffer.

Experimental Method

The Experimental Method is a method of detecting *Listeria* spp. from an environmental sample without the need for an enrichment period. In one embodiment, the method utilizes the ANSR® *Listeria* spp. isothermal nucleic acid amplification assay in conjunction with a modified sample lysis procedure. In some embodiments, the entire collected sample is subjected to the lysis procedure, which is conducted in a small volume of lysis buffer.

In some embodiments, the assay result is read by an automated reader. In other embodiments, the assay result is detected by enzymatic detection methods or gel electrophoresis.

Reference Method

The USDA-MLG protocol for enrichment of *Listeria* in environmental samples was used for culture confirmation. Isolation and Identification of *Listeria monocytogenes* from Red Meat, Poultry and Egg Products, and Environmental Samples (USDA/FSIS Microbiology Laboratory Guidebook, MLG 8.09, Effective May 1, 2013), incorporated by reference herein in its entirety. FIG. 1 demonstrates the key steps in both the Reference Method and Experimental Method. The time to completion for the Experimental Method is approximately 50 minutes, as compared to 3-5 days for the Reference Method.

EXAMPLES

The following examples are offered by way of illustration, not by way of limitation.

Example 1: Culture Confirmation Using USDA-MLG Protocol for *Listeria* Enrichment in Parallel with Experimental Method Samples were collected in parallel and analyzed using both the Experimental Method and the Reference Method. A total of 50-100 environmental swab samples were collected from a processing plant with a goal of at least 20-25 positives using the following protocol:

Sample Collection

1. Collect environmental sample using swabs that are pre-moistened with letheen broth. Hold two swabs together side-by-side and sample the area to be tested.

2. Keep the paired swab samples together and hold at 2-8° C. until testing. Testing should be conducted within 24 hours, preferably the same day as collection.

Experimental Method Sample Preparation

1. Label the appropriate number of microcentrifuge tubes and place in a rack.

2. Prepare ANSR® lysis reagent solution by reconstituting 1 vial of lyophilized lysis reagents with 18 mL of lysis buffer by adding the buffer to the reagent vial; the lyophilized lysis reagents include potassium phosphate, lysozyme and proteinase K, and the lysis buffer includes sodium sulfate, magnesium sulfate and poly(ethylene oxide) octylphenyl ether. Swirl gently to mix. a. One vial of lysis reagents is enough for approximately 18 samples. Prepared lysis reagent solution can be stored at 2-8° C. for 30 days.

3. Add 1 mL of prepared lysis reagent solution to each microcentrifuge tube.

4. Place one swab from each pair into the microcentrifuge tube, swirl and mix gently with up and down movement in the liquid for several seconds.

5. Remove swab from the microcentrifuge tube and discard.

6. Cap tubes and proceed to ANSR Test Procedure (Section D).

Experimental Method Test Procedure

1. Preheat the first lysis heater block to 37±2° C. and the second lysis heater block to 80±2° C.

2. Start the ANSR software using the computer connected to the ANSR reader.

3. Enter sample IDs and experiment information. The reader will preheat to 56±1° C.

4. Add 500 µL of the extracted swab sample to separate 1.2 mL cluster tubes using 1000 µL pipette tips. a. Use a new pipette tip for each sample.

5. Incubate the cluster tubes at 37±2° C. for 10 minutes.

6. Then transfer the cluster tubes to the 80±2° C. heater block and incubate for 20 minutes. a. Note: The incubation time for this step can be extended to a maximum of 60 minutes.

7. At least 3 minutes before the end of the lysis step, preheat the capped ANSR reaction tubes by placing them in the ANSR reader.

8. At the end of the 20 minute 80° C. lysis, remove and discard the caps from the ANSR reaction tubes, which was placed in the ANSR reader.

9. With the cluster tubes still in the 80° C. lysis block, use an 8-channel pipette and 100 µL filtered tips, transfer 50 µL of the lysed sample to the designated reaction tubes in the ANSR reader. Place the permanent caps on the ANSR reaction tubes.

10. After capping, remove the tubes from the reader and vortex briefly (~2 seconds) then place back into the reader without delay. Close the lid of the ANSR reader.

11. Press START on the ANSR software to begin the assay.

12. Results indicating the presence or absence of *Listeria* spp. will be displayed in 18 minutes. Any tests producing invalid results should be repeated.

Reference Method Primary Enrichment in UVM Broth

Add 225±5 ml (or 225±5 g) of UVM broth to each sample. Hand mixing is an acceptable alternative for stomaching. To hand mix, briefly massage each sponge to expel the collection broth into the UVM broth. Incubate at 30±2° C. for 20-26 h.

Reference Method Secondary Enrichment in FB or MOPS-BLEB and Primary Enrichment Plating of UVM a. Transfer 0.1±0.02 ml of the UVM enrichment to 10±0.5 ml of FB or MOPS-BLEB. As per media preparation instructions, be sure that appropriate supplements have been added to the FB prior to inoculation. Incubate inoculated FB tubes at 35±2° C. for 26±2 h or inoculated MOPSBLEB tubes at 35±2° C. for 18-24 h.

b. Streak a MOX plate. Streak a loopful or a drop approximating 0.1 ml of the UVM over the surface of the plate. Alternatively, dip a sterile cotton-tipped applicator or equivalent into the UVM and swab 25-50% of the surface of a MOX plate. Use a loop to streak for isolation from the swabbed area onto the remainder of the plate. Incubate the MOX at 35±2° C. for 26±2 h.

Reference Method Examination of UVM-Streaked MOX, Interpretation/Plating of 26-h FB, and Plating of MOPS-BLEB Examine the UVM-streaked MOX for colonies with morphology typical of *Listeria* spp. At 26±2 h, suspect colonies are typically small (ca. 1 mm) and are surrounded by a zone of darkening due to esculin hydrolysis.

i. If suspect colonies are present on MOX, transfer suspect colonies to HL agar.

ii. If no suspect colonies are evident, re-incubate the MOX plate for an additional 26±2 hour.

iii. Proceed to step b below for FB or step c for MOPS-BLEB.

b. After 26±2 h of incubation, examine the FB for the potential presence of *Listeria monocytogenes*, by visual examination of the broth for darkening due to esculin hydrolysis.

i. If any degree of FB darkening is evident, aseptically dispense a drop approximating 0.1±0.02 ml of FB onto a MOX plate. Swab or streak 25-40% of the surface of the MOX plate with the FB inoculum. Use a loop to streak for isolation from the initial swab/streak quadrant onto the remainder of the plate. Incubate the MOX plate at 35±2° C. for 26±2 h.

ii. If no FB darkening is evident, re-incubate the FB at 35±2° C. until a total incubation time of 48±2 h has been achieved.

c. After 18-24 h, streak a MOX plate using a loopful of the MOPS-BLEB, or by streaking a drop approximating 0.1 ml, or aseptically dip a sterile cotton-tipped applicator or equivalent into the MOPS-BLEB and swab 25-50% of the surface of a MOX plate. Use a loop to streak for isolation from the swabbed area onto the remainder of the plate. Incubate the MOX at 35±2° C. for 26±2 h.

Reference Method Examination of MOX Plates and Interpretation/Plating of 48 h FB a. Examine and select suspect colonies from any MOX agar plate pending analysis (i.e. MOX plates streaked from 26±2 h FB, 18-24 h MOPSBLEB, and/or UVM).

b. Re-examine the FB for evidence of darkening after 48±2 h of total incubation.

i. If any degree of darkening is evident, swab, streak and incubate a MOX plate.

ii. If no darkening of FB is evident and no suspect MOX and/or HL colonies have been demonstrated, the sample is considered negative for *L. monocytogenes*.

Reference Method Isolation and Purification Procedures a. If suspect colonies are present on MOX from any source, use a loop or equivalent sterile device to contact a minimum of 20 (if available) suspect colonies and collectively streak for isolation on one or more HL agar plates. Alternatively, a swipe of suspect growth representing at least 20 colonies may be used. Incubate the streaked HL at 35±2° C. for 22±4 h.

b. After incubation, examine the HL plate(s) against backlight for translucent colonies surrounded by a small zone of β-hemolysis.

i. If at least one suspect colony is clearly isolated, proceed to confirmatory testing (Section 8.6 below). Hold all HL plates containing suspect colonies (room temperature or refrigeration) until confirmatory testing is complete.

ii. If suspect colonies or β-hemolytic growth are present on HL but not clearly isolated, re-streak representative suspect colonies/growth onto one or more fresh HL plates and incubate.

iii. If no suspect isolates are present on HL, pursue follow-up of MOX and/or HL isolates from other branches of analysis (e.g. FB follow-up vs. UVM Primary Enrichment streak follow-up). If no branch of the analysis produces suspect β-hemolytic colonies on HL, the sample may be reported as negative for *L. monocytogenes*.

Results for Test Sites 1-7 are shown in FIGS. 2-9. Overall data showed 88.1% Assay Agreement.

Example 2: Surface Inoculation (Plastic), Compared with USDA Method

ANSR vs. USDA Method

Environmental samples were collected and half of the swabs at each level were expressed directly into 450 μl of ANSR® lysis buffer, assayed immediately on ANSR® *Listeria*. The remaining swabs were added to 10 ml UVM for USDA reference method. Results are shown in tables 1 and 2.

TABLE 1

Surface Inoculation (Plastic), Compared with USDA Method

| Sample | N | CFU/square | ANSR (+) | USDA (+) |
|---|---|---|---|---|
| Unspiked surface | 5 | 0 | 5 | 0 |
| DE blank | 5 | N/A | 3* | 0 |
| $10^{-8}$ | 5 | 6.17E−01 | 4* | 0 |
| $10^{-7}$ | 5 | 6.17E+00 | 5 | 0 |
| $10^{-6}$ | 5 | 6.17E+01 | 5 | 0 |
| $10^{-5}$ | 5 | 6.17E+02 | 5 | 0 |
| $10^{-4}$ | 5 | 6.17E+03 | 5 | 1 |
| $10^{-3}$ | 5 | 6.17E+04 | 5 | 0 |
| $10^{-2}$ | 5 | 6.17E+05 | 5 | 5 |
| Undilute | 5 | 6.17E+07 | 5 | 5 |

*one invalid result

DE blank: 50 μl assayed directly, no contact with surface or swab

TABLE 2

Surface Inoculation (Ceramic) Compared with USDA Method

| Sample | N | CFU/square | ANSR (+) | USDA (+) |
|---|---|---|---|---|
| DE BLANK | 5 | N/A | 0 | 0 |
| BPB BLANK | 5 | N/A | 0* | 0 |
| Unspiked surface | 5 | 0 | 1* | 0 |
| $10^{-8}$ | 5 | 2.06E+00 | 4 | 0 |
| $10^{-7}$ | 5 | 2.06E+01 | 5 | 0 |
| $10^{-6}$ | 5 | 2.06E+02 | 5 | 0 |
| $10^{-5}$ | 5 | 2.06E+03 | 5 | 0 |
| $10^{-4}$ | 5 | 2.06E+04 | 5 | 0 |
| $10^{-3}$ | 5 | 2.06E+05 | 5 | 0 |
| $10^{-2}$ | 5 | 2.06E+06 | 4 | 5 |
| Undilute | 5 | 2.06E+08 | 4* | 5 |

*one invalid in set of five replicates

BPB BLANK; surface inoculated with BPB and swabbed

DE BLANK; 50 μL assayed directly - no contact with surface or swab

Example 3: Surface Swab Samples Using 1 ml Lysis Buffer Verses MOX Streaking Method Surface was spiked with pure *Listeria monocytogenes* culture and environmental samples were subjected to the Experimental Method or streaking on MOX followed by ANSR® *Listeria*. The results are shown in tables 3-6.

TABLE 3

Surface Spiked with Pure Culture

| Sample ID | Lm CFU/area | Experimental Method | LESS Plus ANSR *Listeria* | MOX |
|---|---|---|---|---|
| BPW | 0 | pos* | neg | neg |
|  |  | neg | neg | neg |
| Lm-8 | ~1 | pos | pos | neg |
|  |  | pos | pos | neg |
| Lm-7 | ~10 | pos | pos | neg |
|  |  | pos | pos | neg |
| Lm-6 | ~100 | pos | pos | neg |
|  |  | pos | pos | neg |

TABLE 3-continued

Surface Spiked with Pure Culture

| Sample ID | Lm CFU/area | Experimental Method | LESS Plus ANSR Listeria | MOX |
|---|---|---|---|---|
| Lm-5 | ~1000 | pos | pos | pos | pos |
|  |  | pos | pos | pos | pos |
| Lm-4 | ~10000 | pos | pos | pos | pos |
|  |  | pos | pos | pos | pos |
| Lm-3 | ~100000 | pos | pos | pos | pos |
|  |  | pos | pos | pos | pos |

TABLE 5-continued

Surface Spiked with Lm in Food Matrix, Treated with Bleach

| | | | Before Bleach | | After Bleach | |
| sample # | spiking level | CFU/ area | ANSR | MOX | ANSR | MOX |
|---|---|---|---|---|---|---|
| 4 |  |  | neg | neg | neg | neg |
| 5 | −4 | ~2 | pos | neg | pos | neg |
| 6 |  |  | pos | neg | pos | neg |
| 7 | −3 | ~20 | pos | pos | pos | neg |
| 8 |  |  | pos | pos | neg | neg |
| 9 | −2 | ~200 | pos | pos | pos | neg |
| 10 |  |  | pos | pos | pos | neg |
| 11 | −1 | ~2000 | pos | pos | pos | neg |
| 12 |  |  | pos | pos | pos | neg |

TABLE 6

Surface Spiked with Lm in Food Matrix, Treated with Sanitizers

| | | | Experimental Method ANSR Listeria | | | | Culture Method MOX | | | |
| sample # | spiking level | CFU/ area | no sanizitier | Mandate plus | XY-12 | SterBac | no sanizitier | Mandate plus | XY-12 | SterBac |
|---|---|---|---|---|---|---|---|---|---|---|
| 1 | unspiked | 0 | neg | NA | NA | NA | neg | NA | NA | NA |
| 2 |  |  | neg | NA | NA | NA | neg | NA | NA | NA |
| 3 | −5 | ~0.3 | pos | neg | pos | neg | neg | neg | neg | neg |
| 4 |  |  | pos | neg | neg | neg | neg | neg | neg | neg |
| 5 | −4 | ~3.3 | pos | neg | pos | neg | pos | neg | neg | neg |
| 6 |  |  | neg | neg | neg | pos | pos | neg | neg | neg |
| 7 | −3 | ~33 | pos | pos | pos | pos | pos | neg | neg | neg |
| 8 |  |  | pos | pos | pos | pos | pos | neg | neg | neg |

TABLE 4

Surface Spiked with Listeria monocytogenes in Food Matrix

| | | | Experimental Method | | Culture Method |
| sample # | spiking level | CFU/ area | ANSR Listeria | MOX | MOX |
|---|---|---|---|---|---|
| 1 | unspiked | 0 | neg | neg | neg |
| 2 |  |  | pos/neg | neg | neg |
| 3 | −5 | ~0.05 | neg | neg | neg |
| 4 |  |  | neg | neg | neg |
| 5 | −4 | ~0.5 | neg | neg | neg |
| 6 |  |  | pos | neg | neg |
| 7 | −3 | ~5 | pos | neg | neg |
| 8 |  |  | pos | neg | neg |
| 9 | −2 | ~49 | pos | neg | neg |
| 10 |  |  | pos | neg | neg |
| 11 | −1 | ~490 | pos | pos | pos |
| 12 |  |  | pos | neg | pos |

TABLE 5

Surface Spiked with Lm in Food Matrix, Treated with Bleach

| | | | Before Bleach | | After Bleach | |
| sample # | spiking level | CFU/ area | ANSR | MOX | ANSR | MOX |
|---|---|---|---|---|---|---|
| 1 | unspiked | 0 | neg | neg | neg | neg |
| 2 |  |  | neg | neg | neg | neg |
| 3 | −5 | ~0.2 | neg | neg | neg | neg |

What is claimed is:

1. A method for detecting *Listeria* spp. in an environmental sample, the method comprising the steps of:
   collecting an environmental sample with a collection device;
   expressing the collection device in a lysis reagent solution comprised of sodium sulfate, magnesium sulfate, poly(ethylene oxide)octylphenyl ether, potassium phosphate, lysozyme, and proteinase K; and
   performing a pathogen diagnostic assay that targets bacterial RNA sequences for amplification and detection of *Listeria* RNA in the sample.

2. The method of claim 1, wherein the pathogen diagnostic assay utilizes isothermal amplification of the RNA.

3. The method of claim 1, further comprising, determining that the environmental sample is positive for *Listeria* RNA.

4. The method of claim 1, further comprising, determining that the environmental sample is negative for *Listeria* RNA.

5. The method of claim 1, wherein the collection device is a swab.

6. The method of claim 5, wherein the swab is cotton or polyester.

7. The method of claim 1, wherein the collection device is a sponge.

8. The method of claim 1, wherein the time from collection of the sample to completion of the pathogen diagnostic assay is 1.5 hours or less.

9. The method of claim 1, wherein the assay is an isothermal amplification assay of sufficient sensitivity to detect as little as 1-2 CFU in the environmental sample.

10. The method of claim 1, wherein the volume of lysis reagent solution is about 1.0 ml.

11. The method of claim 10, wherein about 0.5 ml of the sample in lysis reagent solution is used for the pathogen diagnostic assay.

12. The method of claim 1, wherein the collection device is pre-moistened with letheen broth.

* * * * *